(12) United States Patent
Scheiner

(10) Patent No.: US 7,912,550 B2
(45) Date of Patent: Mar. 22, 2011

(54) CLOTHING ATTACHMENT DEVICE FOR AN EXTERNAL COMPONENT OF A MEDICAL DEVICE

(75) Inventor: Rupert Christian Scheiner, Davidson (AU)

(73) Assignee: Cochlear Limited, Macquarie University (AU)

( * ) Notice: Subject to any disclaimer, the term of this patent is extended or adjusted under 35 U.S.C. 154(b) by 1029 days.

(21) Appl. No.: 10/516,891

(22) PCT Filed: Jun. 2, 2003

(86) PCT No.: PCT/AU03/00689
§ 371 (c)(1),
(2), (4) Date: May 31, 2005

(87) PCT Pub. No.: WO03/101349
PCT Pub. Date: Dec. 11, 2003

(65) Prior Publication Data
US 2005/0263549 A1    Dec. 1, 2005

(30) Foreign Application Priority Data
Jun. 3, 2002   (AU) .......................................... PS2742

(51) Int. Cl.
*A61N 1/00* (2006.01)
(52) U.S. Cl. ............... 607/55; 224/182; 224/269; 607/2
(58) Field of Classification Search .................. 24/3.12, 24/10 A, 704, 704.1, 706.2, 206.3; 224/182; 403/348, 353; 607/14, 45, 55–57
See application file for complete search history.

(56) References Cited

U.S. PATENT DOCUMENTS

| | | | |
|---|---|---|---|
| 3,430,829 A * | 3/1969 | Wilson et. al. | 224/182 |
| 3,858,280 A * | 1/1975 | Martens | 70/57.1 |
| 4,146,302 A | 3/1979 | Jachimowicz | |
| 4,156,302 A | 5/1979 | Van Niel | |
| 4,280,256 A * | 7/1981 | de Jong | 24/706.8 |
| 4,322,585 A * | 3/1982 | Liautaud | 381/151 |
| 4,499,245 A | 2/1985 | Ikeguchi et al. | |
| 4,532,930 A | 8/1985 | Crosby et al. | |

(Continued)

FOREIGN PATENT DOCUMENTS

DE    4417821    11/1995

(Continued)

OTHER PUBLICATIONS

International Search Report for PCT/AU03/00689 dated Jul. 15, 2003.

(Continued)

*Primary Examiner* — Carl H Layno
*Assistant Examiner* — Pamela M Bays
(74) *Attorney, Agent, or Firm* — Kilpatrick Townsend & Stockton LLP

(57) ABSTRACT

A mechanism for attaching a component, such as a speech processor unit of a cochlear implant, to the clothing of a user of that component. The attaching mechanism is operable by an unlocking device, such as a magnet that can be held in the possession of a person other than the person wearing the clothing to which the component is mounted. The attachment device can comprise an elongate pin member that is adapted to pass through at least a portion of an item of clothing and be received in a chamber and held by frictional engagement therein.

20 Claims, 6 Drawing Sheets

U.S. PATENT DOCUMENTS

| | | | |
|---|---|---|---|
| 4,993,245 | A | 2/1991 | Ott |
| 5,022,244 | A | 6/1991 | Charlot, Jr. |

FOREIGN PATENT DOCUMENTS

| | | |
|---|---|---|
| EP | 0455577 | 11/1991 |
| WO | 02/068784 | 9/2002 |
| WO | 02068784 | 9/2002 |
| WO | 03101349 | 12/2003 |

OTHER PUBLICATIONS

International Preliminary Examination Report for PCT/AU03/00689 dated Jan. 16, 2004.

International Searching Authority, "International Search Report," issued in connection with International Patent Application No. PCT/AU2003/000689, dated Jul. 15, 2003 (3 pages).

\* cited by examiner

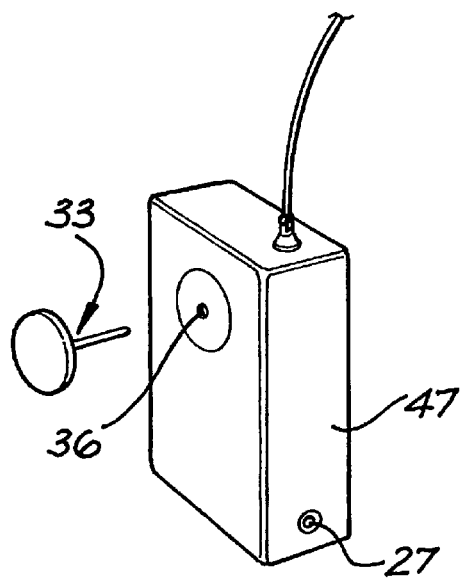
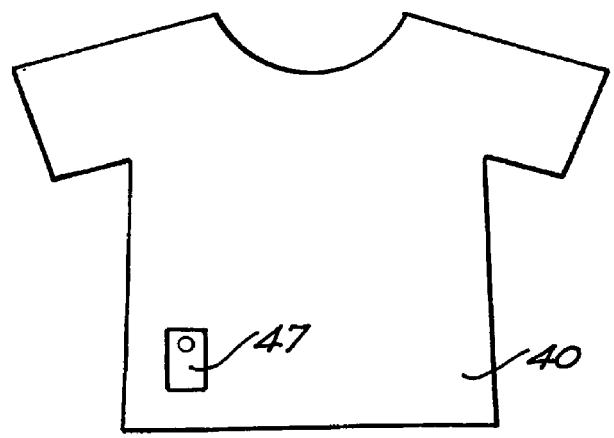
FIG. 6A	FIG. 6B
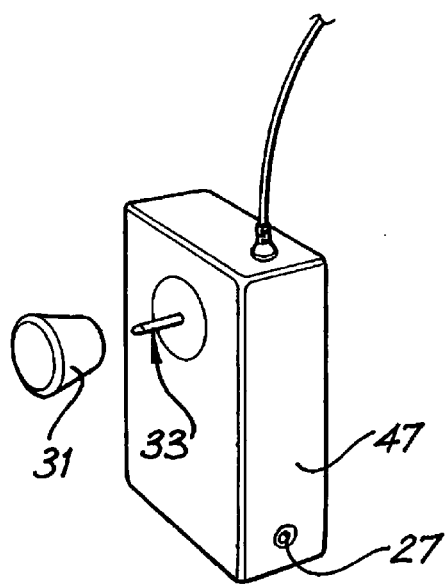
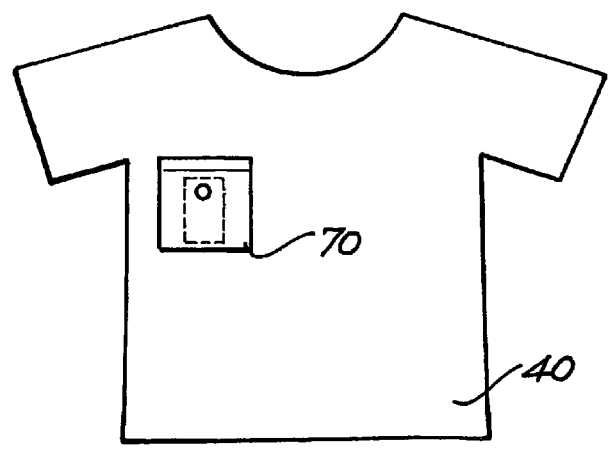
FIG. 7A	FIG. 7B

CLOTHING ATTACHMENT DEVICE FOR AN EXTERNAL COMPONENT OF A MEDICAL DEVICE

TECHNICAL FIELD

The present invention relates to a medical device and more particularly, to a medical prosthesis.

BACKGROUND ART

The application of medical devices, such as hearing aids, implantable pacemakers, defibrillators, cochlear implants and other such functional electrical stimulation devices, are becoming more widespread as their advantages and benefits become more widely appreciated throughout the population.

In particular, cochlear implants have been developed to assist people who are profoundly deaf or severely hearing impaired, by enabling them to experience hearing sensation representative of the natural hearing sensation. In most such cases, these individuals have an absence of or destruction of the hair cells in the cochlea which naturally transduce acoustic signals into nerve impulses which are interpreted by the brain as sound. The cochlear implant therefore bypasses the hair cells to directly deliver electrical stimulation to the auditory nerves with this electrical stimulation being representative of the sound.

Cochlear implants have traditionally consisted of two main parts: an internal part and an external part. The external part includes a speech processor unit and a transmitter coil. The internal part includes an implanted receiver/stimulator unit and an electrode array. The external speech processor unit is typically carried in a pouch or removably clipped on the clothing, such as a belt, worn by the user using a clip. Its main purpose has been to detect sounds using a microphone and then convert the detected sound into a coded signal through an appropriate speech processing strategy.

This coded signal is then sent to the receiver/stimulator unit, which is typically implanted in the mastoid bone of the user, via a transcutaneous radio frequency link. The receiver/stimulator unit processes this coded signal and outputs a series of stimulation sequences. These sequences are transmitted to appropriate electrodes of an electrode array by respective electrically conducting wires. The array is positioned proximal to the modiolus of the cochlea such that an electrical stimulus output by the electrodes is then applied to the auditory nerve.

For infants born with sensorineural hearing loss, studies indicate that it is desirable to implant a cochlear implant as soon as possible after birth. This is because if an infant is to develop an ability to understand and process sounds such as speech, the brain must learn to receive and process signals representative of sounds in the first few years of life.

A problem with infants and even small children is that small children are not aware of the importance of their external speech processor unit and often do not notice when the unit has become detached from their clothing. Children are also naturally inquisitive and as they get older will often detach the speech processor unit from their clothing to examine the unit or pass it among their friends. This often results in the unit being mislaid. When a group of children having cochlear implants play together it is also not unknown for these children to detach their external speech processor units and swap them with those of their friends. As the units are programmed to meet the hearing needs of that particular child, this often results in the unit being reported as faulty by the parents or guardian of the child when in fact the child no longer has their original unit. Further, the child can experience pain and discomfort as a result of using a speech processor that has not been programmed for their particular needs. Further, as children are typically active, it is not uncommon for their external units to be dislodged during regular activity, which can result in the child losing the unit or the unit becoming damaged or destroyed upon dislodgement. As replacement units are expensive and not readily available, such loss or damage can result in the child being without the benefit of the device for extended periods of time until a replacement unit is available.

With regard to adults, it is common for many adult cochlear implant recipients to prefer to use a body-worn external processor for particular conditions, such as in a work or home environment, as opposed to a behind-the-ear processor which is more preferable when mobility and aesthetics is an issue. One of the main problems with body-worn processors is that they are often attached to the body by way of a removable fastener, for example, a belt clip. Whilst such an attachment mechanism allows the device to be easily removed when needed, it can also be uncomfortable to wear and can often be inadvertently dislodged through normal body movements, which can cause unnecessary irritation to such recipients. Further, a dropped processor can be very easily damaged, resulting in inconvenience to the user while the unit is being repaired.

It is desirable to improve upon the above identified shortcomings.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

DISCLOSURE OF INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present invention is directed to a mechanism for attaching a component to the clothing of a user of that component. In particular, the mechanism is operable by an unlocking device that can be held in the possession of a person other than the person wearing the clothing to which the component is mounted.

In one aspect, the present invention is a clothing attachment device for an external component of a hearing prosthesis, the attachment device comprising:
  an elongate member adapted to pass through at least a portion of an item of clothing; and
  a receiving means adapted to receive at least a portion of the elongate member and releasably engage therewith;
  wherein at least one of said elongate member and said receiving means are mountable to the external component and the engagement of said elongate member and said receiving means is releasable by an unlocking device.

In another aspect, the present invention is an external component of a hearing prosthesis, the external component comprising:
  a casing;

a receiving means mounted to the casing; and an elongate member adapted to pass through at least a portion of an item of clothing and be received in the receiving means and releasably engage therewith;

wherein the engagement of said elongate member and said receiving means is releasable by an unlocking device.

In a still further aspect, the present invention is an external component of a hearing prosthesis, the external component comprising:

a casing;

an elongate member extending outwardly from the casing and adapted to pass through at least a portion of an item of clothing; and a receiving means adapted to receive at least a portion of the elongate member and releasably engage therewith;

wherein the engagement of said elongate member and said receiving means is releasable by an unlocking device.

In these aspects, the hearing prosthesis preferably comprises a cochlear implant. In this case, the external component preferably comprises a speech processor unit for receiving signals from a microphone and converting the detected sound into a coded signal through an appropriate speech processing strategy.

In one embodiment, the elongate member can comprise a pin member extending from a proximal end to a distal end. Where the elongate member extends outwardly from the casing of the external component, the pin can be integrally connected to the casing, permanently mounted thereto, or releasably mountable thereto.

In another embodiment, the elongate member can comprise a head and a pin member extending from the head to a distal end.

Where the elongate member has a head, the head can be formed integrally with the pin member or formed separately and then attached thereto. The pin member is preferably formed of a metal, such as stainless steel. The head can be formed of a metal and/or a plastics material.

In one embodiment, the head comprises a disc, such as a circular disc, having a diameter greater than that of the pin member. The head member preferably has a diameter at least 10 and preferably greater than 20 times the diameter of the pin member. The disc is preferably relatively flat and has an underside that is adapted, in use, to be positioned against the clothing.

The distal end of the pin member can have a tapered or pointed end to assist in the passage of the pin member through an item of clothing. It is also envisaged that the distal end of the pin member could also be blunt or rounded in certain situations, for example to avoid sharp implements being used with regard to young children.

In a preferred embodiment, the receiving means is adapted to be mounted to the casing of the speech processor unit of the hearing prosthesis. In one embodiment, the receiving means can be non-removably mounted to the casing. In another embodiment, the receiving means can be removably mounted to the casing.

The receiving means preferably comprises an orifice extending into the receiving means from a front surface thereof. The orifice is able to receive at least a portion of the length of the elongate member. The orifice extends from the front surface to a chamber within the receiving means. The orifice can be tubular. In another embodiment, the orifice can be circular in cross-section.

The chamber of the receiving means preferably has an inner wall of which at least a portion thereof is frusto-conical such that the chamber expands in diameter away from the front surface of the receiving means. In a preferred embodiment, the inner wall is frusto-conical over its entire length from a forward end to a rearward end of the chamber.

The receiving means can further comprise a pin engagement mechanism adapted to frictionally engage the pin member on insertion of the pin member through the orifice and into the chamber.

In one embodiment, the pin engagement mechanism can comprise a plurality of engagement members disposed in at least a substantially circular arrangement within the chamber. In one embodiment, the engagement members can comprise spherical members or balls, such as ball bearings. At least one, and preferably all, of the spherical members or balls are preferably formed from a metallic material, still more preferably a magnetic material. The engagement members, such as the spherical members, are preferably normally positioned in an engaging configuration within the chamber. This configuration is preferably provided by a biasing means positioned within the chamber and which when in its relaxed condition displaces the engagement members towards the forward end of the chamber. The frusto-conical wall of the chamber serves to compress the engagement members towards each other as they are biased towards the front surface of the receiving means. On insertion of the pin member into the receiving means, the pin member can be inserted between the respective inwardly facing surface portions of the engagement members. The members in the engaging configuration do though provide sufficient frictional engagement with the pin member to prevent its withdrawal therefrom by at least a child, and even preferably an adult.

In one embodiment, the biasing means can comprise a spring, such as a spiral spring. The spring is preferably adapted to urge a plate against the engagement members within the chamber and so hold them in the engaging configuration. In one embodiment, the spring is mounted between the rearward end of the chamber and the plate, the plate being mounted to the forward end of the spring. In another embodiment, the biasing means can comprise a compressible elastomeric material.

As defined, an unlocking device is used to disengage the elongate member from the receiving means. In one embodiment, such as where the receiving means utilises the engagement members to provide frictional engagement with the pin member, the unlocking device can comprise a magnet that can be brought adjacent the rearward surface of the receiving means. The magnet preferably has a magnetic field of a strength sufficient to overcome the bias provided on the spheres by the biasing means and so cause the metallic engagement members to move rearwardly relative to the chamber. As the members move relatively rearwardly, the increase in diameter of the chamber serves to allow them to move relatively apart and so remove the frictional engagement between them and the pin member and allowing the pin member to be withdrawn from the receiving means.

Where the hearing prosthesis is being worn by a child, the magnet may be kept in the possession of a supervising adult, such as a parent or guardian. When the external component is to be removed from the clothing, the magnet can be retrieved, and used to disengage the pin member from the receiving means. When the prosthesis is to be used again, the option is open to pass the elongate member through an item of clothing and then into the orifice and chamber of the receiving means. It is preferred that the bias provided by the biasing means is of a strength that allows a typical adult to insert the pin into the receiving means with the result that it is engaged by the engagement members without the necessity to firstly use the magnet to withdraw the members prior to insertion. It will be appreciated that in another embodiment, this could be a requirement for successfully engaging the pin member to the receiving means.

In accordance with another aspect of the present invention, there is provided an external component of a medical device, the external component comprising:
  a casing;
  an elongate member having a disc and a pin member adapted to pass through at least a portion of an item of clothing; and
  a pin member engagement device having a plurality of spheres disposed in a circular arrangement within a chamber, the chamber having an inner wall, of which at least a portion is frusto-conical such that the chamber expands in diameter away from a front surface of the engagement device, the pin engagement device also having a spring acting and mounted between a rearward end of the chamber and a plate, the spring being adapted to urge the plate against the spheres within the chamber;
  wherein an orifice is formed in the engagement device to enable entry of the pin member into the chamber and thereafter frictionally engage with the plurality of spheres, the engagement of the pin being releasable by a magnet having a magnetic field of a strength sufficient to overcome the bias provided on the spheres by the spring and so cause the spheres to move rearwardly relative to the chamber.

In accordance with yet another aspect of this disclosure, there is provided an external component of a medical device, the external component comprising:
  a casing;
  an elongate member extending outwardly from the casing and adapted to pass through at least a portion of an item of clothing; and
  a receiving means adapted to receive at least a portion of the elongate member and releasably engage therewith;
  wherein the engagement of said elongate member and said receiving means is releasable by an unlocking device.

In accordance with yet another aspect of this disclosure, there is provided an external component of a medical device, the external component comprising:
  an elongate member;
  a retaining means for frictionally retaining at least a portion of the elongate member in a first configuration and for releasing the at least one portion in a second configuration; and
  a biasing means for biasing the retaining device into the first configuration;
  wherein the retaining means is incorporated into the external component to enable the external component to be fastened to an item of clothing worn by a user of the external component, when the retaining means is frictionally retaining the at least a portion of the elongate member. Preferably, the elongate member is releasable from the retaining means by momentarily counteracting the biasing means to cause the retaining means to assume the second configuration.

BRIEF DESCRIPTION OF DRAWINGS

By way of example only, a preferred embodiment of the invention is now described with reference to the accompanying drawings, in which:

FIG. 6A is a perspective view of the external speech processor unit of FIGS. 2 to 5;

FIG. 6B is the external speech processor unit of FIG. 6A attached to an item of clothing;

FIG. 7A is a perspective view of an alternative external speech processor unit;

FIG. 7B is the external speech processor unit of FIG. 7A attached to an item of clothing;

BEST MODE FOR CARRYING OUT THE INVENTION

While it is to be understood that the present invention has wider application, the invention will be hereinafter described with reference to its application to mounting a speech processor of a cochlear implant to the clothing of a user of the implant.

Figure 1:
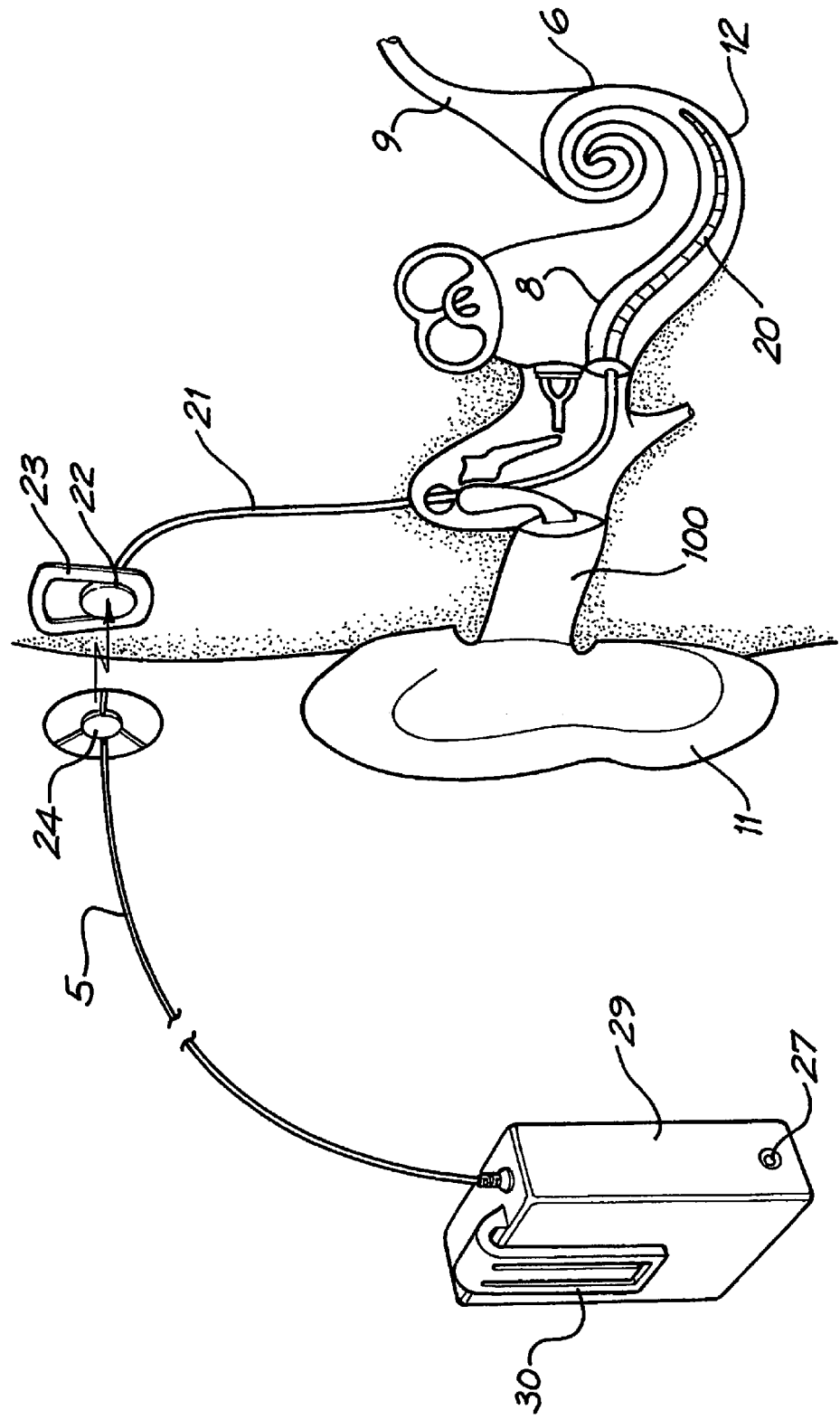
FIG. 1 is a simplified pictorial representation of a prior art cochlear implant system.

Before describing the features of the present invention, it is appropriate to briefly describe the construction of one type of known cochlear implant system with reference to FIG. 1.

A cochlear implant typically consists of two main components, an external component including a speech processor unit 29, and an internal component including an implanted receiver and stimulator unit 22. The external component includes a microphone 27. The speech processor unit 29 is, in this illustration, constructed and arranged to be clipped to the clothing of a recipient with the use of a clip 30, or carried in a pouch worn by the recipient. In the depicted arrangement, a transmitter coil 24 receives signals from the speech processor 29 through cable 5 which in turn transmits signals to the implanted unit 22 via a radio frequency (RF) link.

The implanted component includes a receiver coil 23 for receiving power and data from the transmitter coil 24. A cable 21 extends from the implanted receiver and stimulator unit 22 to the cochlea 6 and terminates in an electrode carrier 20. The signals thus received are applied by the electrodes of the carrier 20 to the basilar membrane 8 thereby stimulating the auditory nerve 9.

Figure 2:
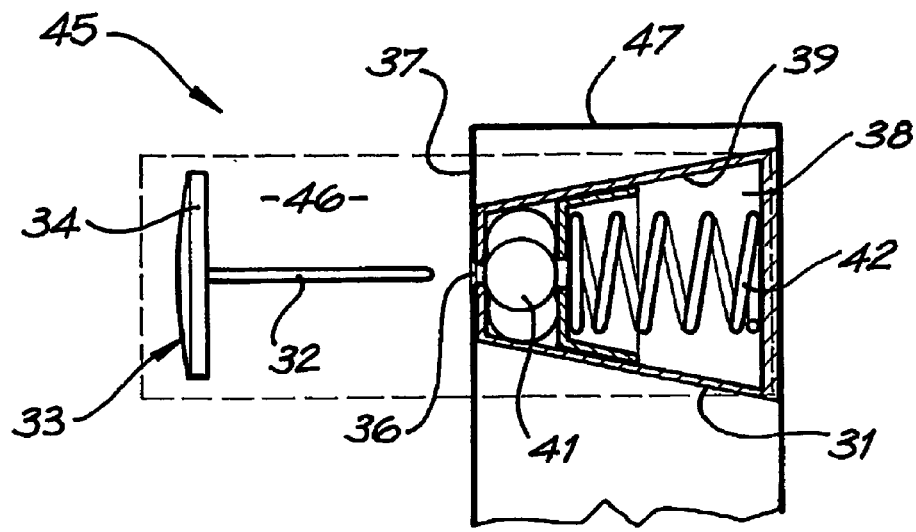
FIG. 2 is a simplified, partial sectional view of one embodiment of a clothing attachment device within an external speech processing unit according to the present invention.

Turning to FIG. 2, a portion of an external speech processor unit 45 having a clothing attachment device 46 is depicted, the clothing attachment device 46 being incorporated into a body or casing 47 of the external speech processor unit 45. The clothing attachment device 46 includes a pin engagement device 31 that is adapted to receive and retain an elongated member in the form of a pin 33. Preferably, the pin 33 is frictionally engaged with the pin engagement device 31. The elongate portion 32 of the depicted pin 33 is formed from stainless steel, with a portion of the elongate portion 32 tapering adjacent to a distal end 35 to assist in passage of the pin 33 through an item of clothing 40. The elongate portion 32 may also be blunt adjacent the distal end 35, to the extent that the weave of an intended clothing fabric will allow the pin to pass through. Such a blunt end could be desirable for the sake of child safety.

As depicted, the pin 33 can have a relatively flat disc-shaped head 34, the outside surface of which normally sits against the skin of the user. The head 34 has the elongate portion 32 extending therefrom to the distal end 35. The head 34 is formed of stainless steel material, however the head 34 could also be formed of a polymeric material or other suitable material. The diameter of the pin head is in the order of 1.25 mm. The depicted head 34 has a diameter at least 10 times that of the diameter of the elongate portion 32 and so is around 12.5 mm diameter.

Figure 3:
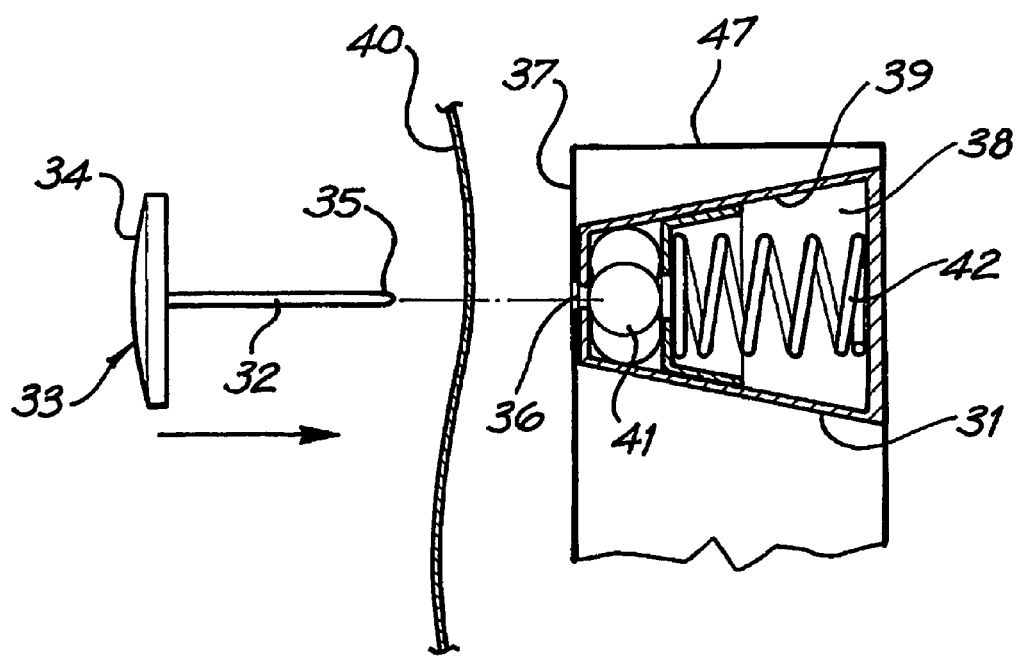
FIG. 3 is a view of the clothing attachment device of FIG. 2 with the external speech processing unit being ready to attach to an item of clothing.

It will be appreciated that in another arrangement, the elongate portion 32 could extend outwardly from the casing 47 of the processor unit 45 with the engagement device 31 being free, as shown in FIG. 7A. This arrangement could be suitable where the external speech processor unit 29 is regularly carried in a pocket 70, as shown for example in FIG. 7B. Referring now to FIG. 3, the pin engagement device 31 has an orifice 36 extending into the processor unit 29 from a front surface 37 of the pin engagement device 31. The pin engagement device 31 is able to receive at least a portion of the length of the elongate portion 32 of the pin 33. As depicted, the orifice 36 extends from the front surface 37 to a chamber 38.

The chamber 38 has a frusto-conical inner wall 39 such that the chamber 38 expands in diameter away from the front surface 37. Disposed within the chamber 38 is a pin engagement mechanism in the form of a plurality of metallic spheres 41, or ball bearings. These spheres 41 are disposed in a generally circular arrangement, although they need not necessarily be all touching one another, within the chamber 38. The spheres 41 are normally positioned toward the front of the chamber 38 in an engaging configuration as is depicted in FIG. 3. This configuration is provided by a biasing spring 42 that is positioned within the chamber 38 and which, when in its relaxed condition, displaces the spheres 41 towards the forward end of the chamber 38. This engaging configuration is maintained regardless of the physical orientation of the attachment device 46, due to the action of the spring 42. The frusto-conical wall 39 of the chamber 38 serves to compress the spheres 41 towards each other as the spheres 41 are pushed by the spring 42 towards the front surface 37. In the depicted embodiment, the front surface 37 is that surface of the attachment device 46 which abuts with the clothing 40.

Figure 4:
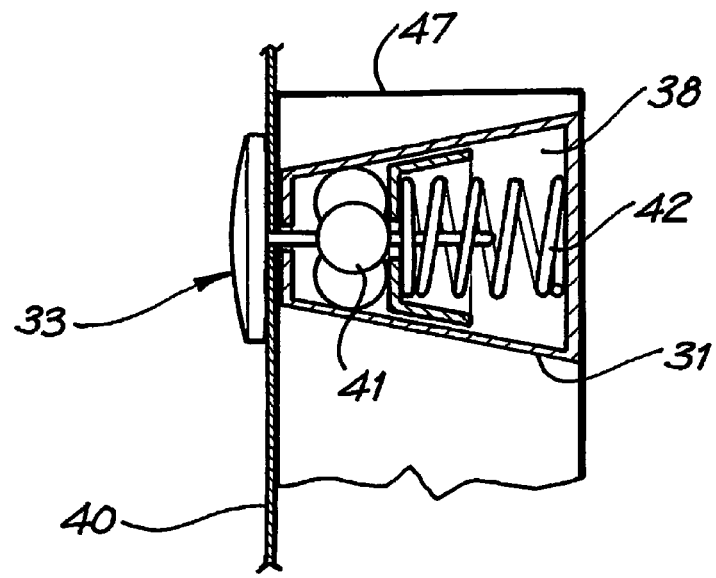
FIG. 4 is a view of the clothing attachment device of FIG. 2 depicting the external speech processor unit of a cochlear implant prosthesis attached to an item of clothing.

On insertion of the elongate portion 32 of the pin 33 into the orifice 36, the elongate portion 32 can be inserted between the respective inner surfaces of the spheres 41. As depicted in FIG. 4, the insertion of the pin 33 results in the spheres 41 being moved relatively rearwardly a relatively small distance within the chamber 38. The spheres 41 are now arranged in the engaging configuration through the biasing action of the spring 42 and provide sufficient frictional engagement with the elongate portion of the pin 33 to prevent its withdrawal therefrom by a child, and even preferably an adult.

As depicted, the spring 42 urges a plate 43 against the spheres 41 within the chamber 38 and so holds the spheres 41 in the engaging configuration, no matter what orientation the chamber is arranged e.g., upside down, sideways or other.

The pin 33 can be incrementally inserted and retained in the pin engagement device 31, thus enabling various different thicknesses of clothing to be used.

Once the pin 33 is inserted into the engagement device 31, it serves to securely fasten of the unit 47 to the clothing 40 as is depicted in FIGS. 4, 6A and 6B.

Figure 5:
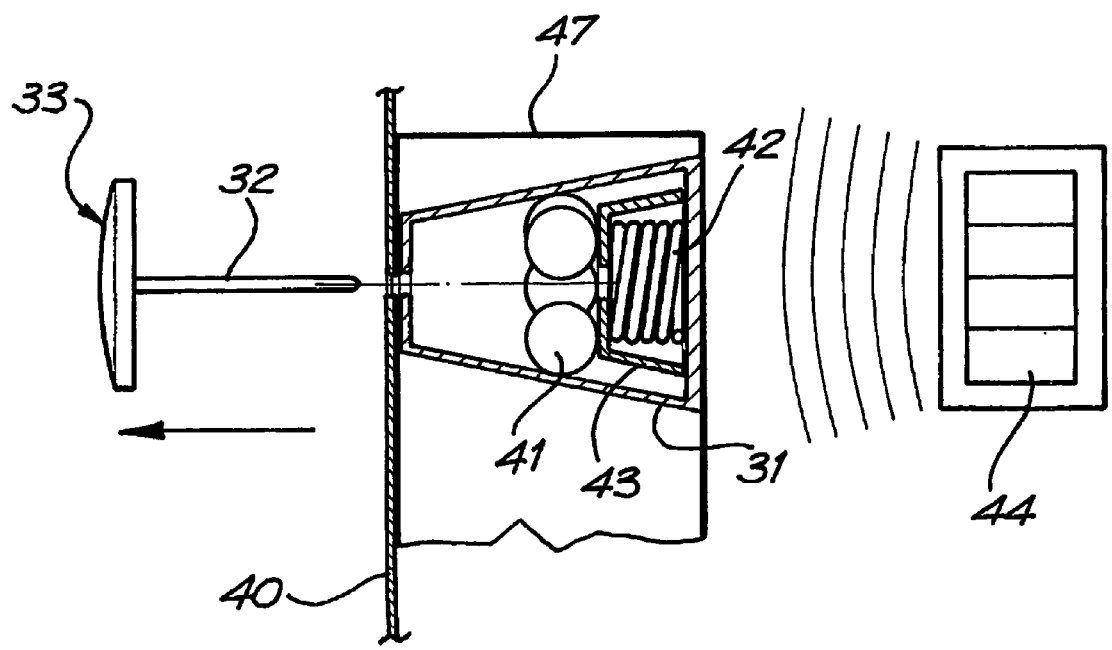
FIG. 5 is a view of the clothing attachment device of FIG. 2 following disengagement of the external speech processor unit from the clothing.

To disengage the pin 33 from the engagement device 31, a magnet 44 can be brought adjacent the rearward end or surface of the device 31 as is depicted in FIG. 5. The magnet 44 is made up of several permanent magnets arranged together in a convenient, portable housing. The magnet 44 has a magnetic field of a strength sufficient to overcome the bias provided on the spheres 41 by the spring 42 and so cause the spheres 41 and the plate 43 to move rearwardly relative to the chamber 38. As the spheres 41 move relatively rearwardly, the increase in diameter of the chamber 38 serves to allow the spheres to also move apart sufficiently to remove the frictional engagement between the spheres 41 and the pin 33 and so allow the pin 33 to be withdrawn from the engagement device 31. The pin engagement device 31 is then ready to be used again when required.

In one example, the strength of magnetic field required by the magnet 44 was in the range of 0.689 kGauss (with 6 mm air gap) to 0.838 k Gauss (with 6 mm air gap). This example used a pin having a head of approximately 12 mm diameter and a pin member of approximately 1.25 mm diameter. Importantly, the magnetic field must be matched to the construction of the pin engagement device 31 so that the biasing action of the spring 42 can be counteracted to the extent required to enable the engagement device 31 to release the pin 33.

Where the cochlear implant is being worn by a child, the magnet 44 can be kept in the possession of a supervising adult, such as a parent or guardian. When the processor unit 45 is to be removed from the clothing 40, the magnet 44 can be retrieved, and used to disengage, or release the pin 33 from the engagement device 31. When the prosthesis is to be used again, the option is open to pass the pin 33 through an item of clothing 40 and then into the orifice 36 and chamber 38. It is preferred that the bias provided by the spring 42 is of a strength that allows a typical adult to insert the pin into the device with the result that it is engaged by the spheres 41 without the necessity to firstly use the magnet 44 to withdraw the spheres 41 prior to insertion. It will be appreciated that in another embodiment, this could be a requirement for successfully engaging the pin 33 to the engagement device 31.

Figure 8A:
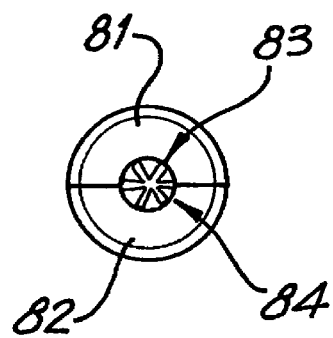
FIGS. 8A to 8D are views of a clothing attachment device according to an alternative configuration.
Figure 8B:
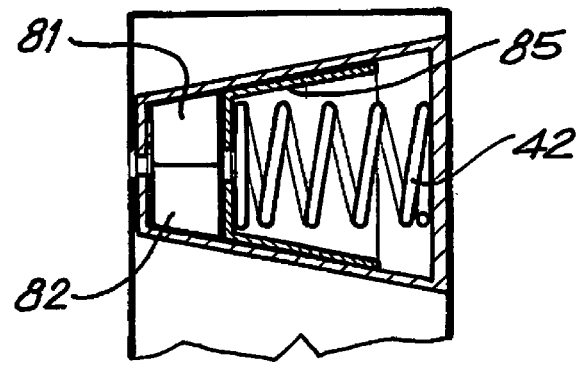
Figure 8C:
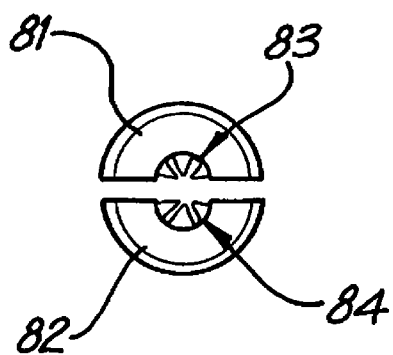
Figure 8D:
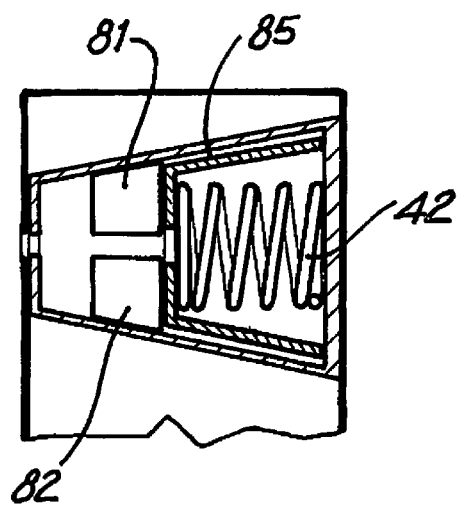

An alternative arrangement is shown in FIGS. 8A to 8D in which the rearward movement of the spring 42 is limited by the dimensions of the plate 85. This allows the plurality of spheres to be replaced with engagement members of a different shape. This is because there is no need for spheres which can naturally realign themselves after being allowed to freely move in the space created at the front of the chamber when the pin is disengaged and the spring is fully counteracted by the magnet. Instead, the plate in FIGS. 8A to 8D limits the space created when the pin is disengaged and thus, the movement of the engagement members is minimised. Accordingly, the pin engagement members of FIGS. 8A to 8D are in the form of a pair of semi-circular elements 81, 82. Thus, when the members are urged together as shown in FIGS. 8A and 8B, a frictional engagement with a pin can be achieved. The limitation of the rearward movement keeps the members 81, 82 aligned and ready to be pushed into the engagement configuration when required.

Figure 9:
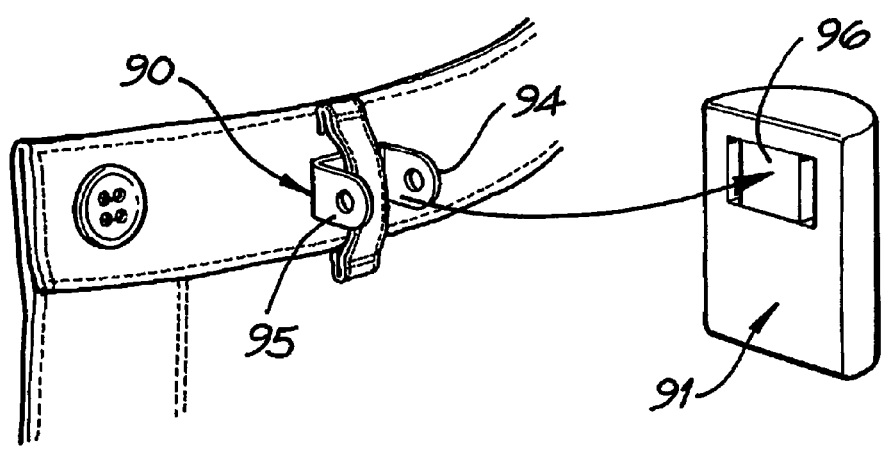
FIG. 9 is a perspective view of an external speech processor unit according to an alternative configuration.

FIG. 9 shows an alternative configuration in which the elongate member comprises one or more flat members 94, 95. In this case, the elongate member is a U-shaped member 90 arranged be slotted into a receiving device 96 co-operatively configured within the speech processor unit 91.

Figure 10:
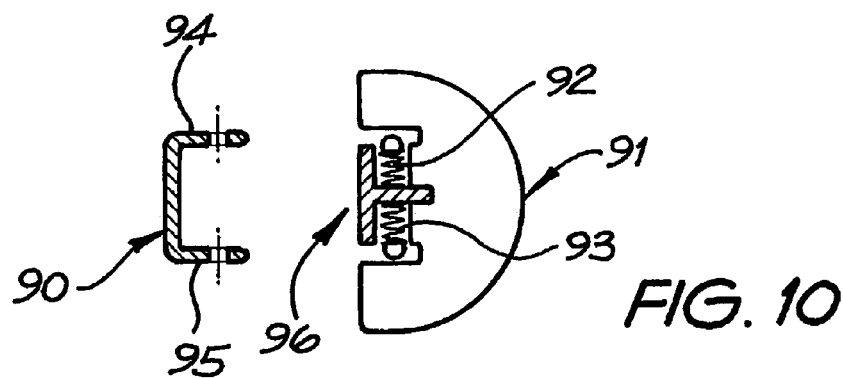
FIG. 10 is a horizontal section through the external speech processor unit of FIG. 9.

Referring to FIG. 10, the biasing means is provided by way of a pair of springs 92, 93, each of which act on a ball bearing at their respective ends. Each of the ball bearings are arranged to engage with a hole in each of the legs of the flat members 94, 95 and thus engage the U-shaped member 90 in the receiving device 96. When it desired to disengage the U-shaped member 90 from the receiving device 96, each spring can be counteracted by the action of an external magnet, thus retracting the ball bearing from the holes 94, 95 and releasing the U shaped member 90.

Figure 11:
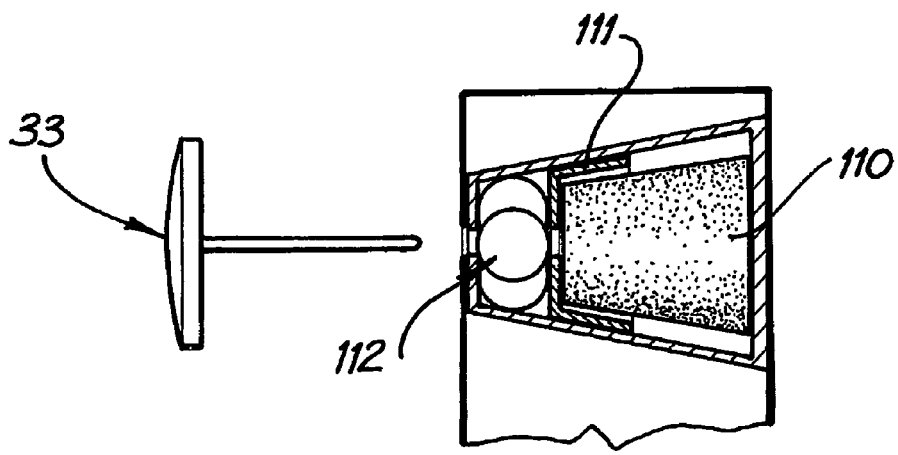
FIG. 11 is a simplified, partial section view of a clothing attachment device according to an alternative configuration.

FIG. 11 shows an alternative configuration to the biasing means, or spring described in relation to FIGS. 2 to 5. In FIG. 11, the spring is replaced with a compressible elastomeric material 110. Since the means by which the biasing occurs is not a magnetic material (unlike the spring, which is preferably metal), the magnetic characteristics of the plate 111 and the pin engagement device 112 need to be taken into account to ensure that the external magnet will exert enough counteractive force to the material 110 to unlock the pin 33.

The mechanism described herein ensures a speech processor unit of a cochlear implant remains in place and secured to the clothing of a child wearer, particularly an infant. This has particular advantage in ensuring the processor unit is not inadvertently lost and also has the potential to reduce the likelihood of damage to the processor unit during normal play and activities of a child or infant.

Further, the mechanism can be made small and relatively unobtrusive to the wearer of the external component.

It will be appreciated by persons skilled in the art that numerous variations and/or modifications may be made to the invention as shown in the specific embodiments without departing from the spirit or scope of the invention as broadly described. For example, the clothing attachment mechanism could be applied to a medical prosthesis such as a pacemaker or other functional electrical systems (FES) such as for spinal stimulation.

The present embodiments are, therefore, to be considered in all respects as illustrative and not restrictive.

The invention claimed is:

1. A cochlear implant comprising:
an implantable component including an implantable elongate electrode carrier; and
an external component including a clothing attachment device for attaching the external component to an article of clothing, the clothing attachment device comprising:
an elongate member adapted to pass through at least a portion of the article of clothing;
an engagement housing;
a plurality of engagement members disposed in the engagement housing and collectively configured to releasably engage at least a portion of the elongate member and configured to release said elongate member from said engagement members in response to the application of a magnetic field to said engagement members,
wherein at least one of said elongate member and said engagement housing is mounted to the external component.

2. The cochlear implant of claim 1, wherein the elongate member is a pin member extending from a proximal end to a distal end.

3. The cochlear implant of claim 2, wherein the pin member extends outwardly from a casing of the external component to its distal end.

4. The cochlear implant of claim 3, wherein the proximal end of the pin member is integrally connected to the casing.

5. The cochlear implant of claim 1, wherein the elongate member comprises a head and a pin member extending from the head to a distal end.

6. The cochlear implant of claim 1, wherein the engagement housing is mounted to a casing of the external component.

7. The cochlear implant of claim 6, wherein the engagement housing comprises an orifice extending into the engagement housing from a front surface thereof, wherein the orifice is configured to receive at least a portion of the length of the elongate member.

8. The cochlear implant of claim 7, wherein the orifice extends from the front surface to a chamber within the engagement housing.

9. The cochlear implant of claim 8, wherein the chamber of the engagement housing has a inner wall of which at least a portion thereof is frusto-conical such that the chamber extends in diameter away from the front surface of the engagement housing.

10. The cochlear implant of claim 9, wherein the non-spherical engagement members are configured to engage the elongate member on insertion of the elongate member through the orifice and into the chamber.

11. The cochlear implant of claim 1, wherein said engagement members are metallic members.

12. The cochlear implant of claim 8, wherein a biasing means is positioned within the chamber and, when in its relaxed condition, displaces the plurality of engagement members towards the front surface of the engagement housing and into the engaging configuration.

13. The cochlear implant of claim 12, wherein the biasing means is a spring and plate, the spring being mounted between a rearward end of the chamber and the plate, and the plate being mounted to a forward end of the spring.

14. The cochlear implant of claim 13, wherein the magnetic unlocking device is a magnet, and the magnetic field has a strength sufficient to overcome the bias provided on the engagement members by the biasing means and so cause the engagement members to move rearwardly relative to the chamber when brought adjacent a rear surface of the engagement housing.

15. A cochlear implant comprising:
an implantable component including an implantable elongate electrode carrier; and
an external component comprising:
a casing;
at least one processor of the cochlear implant disposed in the casing;
an elongate member having a disc and a pin member extending from the disc and configured to pass through at least a portion of an item of clothing; and
a pin member engagement device having a plurality of magnetic spheres disposed in a circular arrangement within a chamber, the chamber having an inner wall, of which at least a portion is frusto-conical such that the chamber expands in diameter away from a front surface of the engagement device, the pin engagement device also having a spring mounted and configured to act between a rearward end of the chamber and a plate, the spring being adapted to urge the plate against the spheres within the chamber;
wherein an orifice is formed in the engagement device to enable entry of the pin member into the chamber, the plurality of spheres are configured to engage the pin member, the engagement of the pin member being releasable by a magnet configured to act on said plurality of magnetic spheres and having a magnetic field of a strength sufficient to overcome a force exerted on the spheres by the spring and to cause the spheres to move rearwardly relative to the chamber.

16. A cochlear implant comprising:
an implantable component; and
an external component comprising:
  a casing;
  an elongate member;
  at least one processor of the cochlear implant disposed in the casing;
  a retaining means for frictionally retaining at least a portion of the elongate member in a first configuration and for releasing the at least a portion in a second configuration; and
  a biasing means for biasing the retaining means into the first configuration;
  wherein the retaining means is configured to enable the external component to be fastened to an item of clothing worn by a user of the cochlear implant when the retaining means is frictionally retaining the at least a portion of the elongate member, and wherein the retaining means is configured to transition from the first configuration to the second configuration upon application of a magnetic field thereto.

17. The cochlear implant of claim 16, wherein the elongate member is releasable from the retaining means by momentarily counteracting the biasing means to cause the retaining means to assume the second configuration.

18. The cochlear implant of claim 17, wherein at least a part of the retaining means comprises a magnetic material and the biasing means is counteracted by applying a magnetic field to the at least a part of the retaining means.

19. The cochlear implant of claim 18, wherein the biasing means is a spiral spring.

20. The cochlear implant of claim 19, wherein the retaining means comprises a plurality of spheres disposed in a substantially circular arrangement within a chamber.

* * * * *